US007315375B2

(12) United States Patent
Van Geen

(10) Patent No.: US 7,315,375 B2
(45) Date of Patent: Jan. 1, 2008

(54) REAGENTS FOR ARSENIC METER

(75) Inventor: Alexander Van Geen, Palisades, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 178 days.

(21) Appl. No.: 11/006,284

(22) Filed: Dec. 7, 2004

(65) Prior Publication Data

US 2005/0118722 A1 Jun. 2, 2005

Related U.S. Application Data

(63) Continuation of application No. PCT/US03/026484, filed on Aug. 21, 2003.

(60) Provisional application No. 60/573,133, filed on May 21, 2004, provisional application No. 60/404,964, filed on Aug. 21, 2002.

(51) Int. Cl.
*G01N 21/25* (2006.01)
(52) U.S. Cl. .................................................. 356/407
(58) Field of Classification Search ................. 356/407
See application file for complete search history.

(56) References Cited

U.S. PATENT DOCUMENTS

| 4,847,066 A * | 7/1989 | Honigs et al. ............. 424/10.3 |
| 6,075,595 A | 6/2000 | Malinen |
| 6,696,300 B1 * | 2/2004 | Jaunakais et al. .............. 436/73 |

OTHER PUBLICATIONS

Johnson, D. L., and M. E. Q. Pilson,"Spectrophotometric Determination of Arsenite, Arsenate, and Phosphate in Natural Waters," Analytica Chimica Acta, 58, p. 289-299, 197.*
Johnson, D. L., "Simultaneous determination of arsenate and phosphate in natural waters," Enviromental Science and Technology, 5, pp. 411-14, 1971.

* cited by examiner

*Primary Examiner*—Roy M. Punnoose
(74) *Attorney, Agent, or Firm*—Baker Botts LLP; Manu J. Tejwani

(57) ABSTRACT

A formulation for preparing water samples for determining arsenic concentration by colorimetry is provided. The chemical reagents in the formulation may be provided as premeasured and premixed tablets or pills. The chemical reagents include sulfamic acid, an oxidizer, and color reagents for selectively forming molybdenum-based color complexes with arsenates and phosphates. To test for arsenic, the water samples are acidified by addition of sulfamic acid. Sulfamic acid also advantageously reduces arsenic to an arsenite state. Arsenic in the water sample is oxidized or re-oxidized to an arsenate state by addition of the oxidizer. Then, color reagents are used to selectively bind and convert arsenates and phosphates in the water samples into molybdenum-blue color complexes. The light absorbance of the water sample with both arsenates and phosphates bound in molybdenum-blue color complexes is compared to that of a reference acidified specimen in which mostly only the phosphates but not the arsenates are bound and converted. The differential light absorbance of the two specimens is used to arrive at a quantitative value for the arsenic concentration in the water sample.

9 Claims, 6 Drawing Sheets

|      | As (ug/L) | Absorbance | Avg    | stdev  | %stdev | Stdev (ug/L As) |
|------|-----------|------------|--------|--------|--------|-----------------|
| Ox   | 0         | 0.1075     | 0.1077 | 0.0002 | 0.19%  | 0.7             |
|      | 0         | 0.1075     |        |        |        |                 |
|      | 0         | 0.1078     |        |        |        |                 |
|      | 0         | 0.1079     |        |        |        |                 |
| Ox   | 80        | 0.1302     | 0.1306 | 0.0003 | 0.26%  | 1.1             |
|      | 80        | 0.1305     |        |        |        |                 |
|      | 80        | 0.1309     |        |        |        |                 |
|      | 80        | 0.1309     |        |        |        |                 |
| Ox   | 160       | 0.1508     | 0.1512 | 0.0003 | 0.19%  | 0.9             |
|      | 160       | 0.1514     |        |        |        |                 |
|      | 160       | 0.1511     |        |        |        |                 |
|      | 160       | 0.1514     |        |        |        |                 |
| Ox   | 240       | 0.1732     | 0.1736 | 0.0004 | 0.22%  | 1.2             |
|      | 240       | 0.1735     |        |        |        |                 |
|      | 240       | 0.1741     |        |        |        |                 |
|      | 240       | 0.1737     |        |        |        |                 |
| Red  | 0         | 0.1079     | 0.1078 | 0.0003 | 0.31%  | 1.1             |
|      | 0         | 0.1074     |        |        |        |                 |
|      | 0         | 0.1077     |        |        |        |                 |
|      | 0         | 0.1082     |        |        |        |                 |
| Red  | 80        | 0.1082     | 0.1089 | 0.0007 | 0.64%  | 2.3             |
|      | 80        | 0.1096     |        |        |        |                 |
|      | 80        | 0.1094     |        |        |        |                 |
|      | 80        | 0.1084     |        |        |        |                 |
| Red  | 160       | 0.1089     | 0.1080 | 0.0007 | 0.61%  | 2.2             |
|      | 160       | 0.1077     |        |        |        |                 |
|      | 160       | 0.1074     |        |        |        |                 |
|      | 160       | 0.1078     |        |        |        |                 |
| Red  | 240       | 0.1099     | 0.1094 | 0.0004 | 0.38%  | 1.3             |
|      | 240       | 0.1094     |        |        |        |                 |
|      | 240       | 0.1093     |        |        |        |                 |
|      | 240       | 0.1089     |        |        |        |                 |

Avg stdev    1.4 ug/L As

FIG. 1

|     | As (ug/L) | Absorbance | Avg | stdev | %stdev | Stdev (ug/L As) |
| --- | --- | --- | --- | --- | --- | --- |
| Ox  |     | 0.1108 | 0.1108 | 0.0003 | 0.24% | 0.9 |
|     | 0   | 0.1111 |     |     |     |     |
|     | 0   | 0.1106 |     |     |     |     |
|     | 0   | 0.1105 |     |     |     |     |
| Ox  | 8   | 0.1115 | 0.1117 | 0.0003 | 0.30% | 1.1 |
|     | 8   | 0.1116 |     |     |     |     |
|     | 8   | 0.1115 |     |     |     |     |
|     | 8   | 0.1122 |     |     |     |     |
| Ox  | 16  | 0.1149 | 0.1145 | 0.0004 | 0.34% | 1.3 |
|     | 16  | 0.1140 |     |     |     |     |
|     | 16  | 0.1144 |     |     |     |     |
|     | 16  | 0.1147 |     |     |     |     |
| Ox  | 24  | 0.1171 | 0.1166 | 0.0004 | 0.32% | 1.2 |
|     | 24  | 0.1166 |     |     |     |     |
|     | 24  | 0.1163 |     |     |     |     |
|     | 24  | 0.1163 |     |     |     |     |
| Red | 0   | 0.1090 | 0.1089 | 0.0000 | 0.05% | 0.2 |
|     | 0   | 0.1089 |     |     |     |     |
|     | 0   | 0.1089 |     |     |     |     |
|     | 0   | 0.1089 |     |     |     |     |
| Red | 8   | 0.1096 | 0.1092 | 0.0003 | 0.26% | 0.9 |
|     | 8   | 0.1091 |     |     |     |     |
|     | 8   | 0.1090 |     |     |     |     |
|     | 8   | 0.1090 |     |     |     |     |
| Red | 16  | 0.1097 | 0.1096 | 0.0001 | 0.13% | 0.5 |
|     | 16  | 0.1096 |     |     |     |     |
|     | 16  | 0.1094 |     |     |     |     |
|     | 16  | 0.1097 |     |     |     |     |
| Red | 24  | 0.1096 | 0.1099 | 0.0005 | 0.42% | 1.5 |
|     | 24  | 0.1094 |     |     |     |     |
|     | 24  | 0.1104 |     |     |     |     |
|     | 24  | 0.1101 |     |     |     |     |

Avg stdev       0.9 ug/L As

FIG. 2

| | As (ug/L) | Absorbance | Avg | stdev | %stdev | Stdev (ug/L As) |
|---|---|---|---|---|---|---|
| Red | 0 | 0.1085 | 0.1084 | 0.0001 | 0.11% | 0.4 |
| | 0 | 0.1083 | | | | |
| | 0 | 0.1085 | | | | |
| | 0 | 0.1083 | | | | |
| Red | 8 | 0.1097 | 0.1096 | 0.0003 | 0.23% | 0.8 |
| | 8 | 0.1096 | | | | |
| | 8 | 0.1099 | | | | |
| | 8 | 0.1093 | | | | |
| Red | 16 | 0.1086 | 0.1090 | 0.0003 | 0.31% | 1.1 |
| | 16 | 0.1089 | | | | |
| | 16 | 0.1094 | | | | |
| | 16 | 0.1091 | | | | |
| Red | 24 | 0.1090 | 0.1087 | 0.0003 | 0.31% | 1.1 |
| | 24 | 0.1090 | | | | |
| | 24 | 0.1086 | | | | |
| | 24 | 0.1083 | | | | |
| Red | 80 | 0.1094 | 0.1091 | 0.0002 | 0.19% | 0.7 |
| | 80 | 0.1091 | | | | |
| | 80 | 0.1089 | | | | |
| | 80 | 0.1091 | | | | |
| Red | 160 | 0.1099 | 0.1102 | 0.0003 | 0.28% | 1.0 |
| | 160 | 0.1100 | | | | |
| | 160 | 0.1106 | | | | |
| | 160 | 0.1101 | | | | |
| Red | 240 | 0.1090 | 0.1091 | 0.0004 | 0.39% | 1.4 |
| | 240 | 0.1086 | | | | |
| | 240 | 0.1093 | | | | |
| | 240 | 0.1096 | | | | |

Avg stdev    0.9 ug/L As

FIG. 3

REAGENTS FOR ARSENIC METER

CROSS-REFERENCE TO RELATED APPLICATION

This application is a continuation of International Patent Application No. PCT/US03/026484 filed on Aug. 21, 2003, which claims priority to U.S. Provisional Patent Applications No. 60/404,964 filed Aug. 21, 2002, both of which are incorporated by reference in their entireties herein. Further, this application claims the benefit of U.S. provisional patent application Ser. No. 60/573,133 filed May 21, 2004, which is also incorporated by reference in its entirety herein.

BACKGROUND OF THE INVENTION

The present invention relates to devices and techniques for measuring arsenic concentrations, and more specifically for quantitative measurements of arsenic concentrations in aqueous solutions. The invention may be used for field measurements of arsenic concentrations in groundwater.

International Patent Application No. PCT/US03/026484, incorporated by reference herein, describes a portable arsenic meter for testing and measuring the arsenic concentrations in samples of ground water. The portable arsenic meter exploits differential infrared measurements of arsenic color complexes formed in test water samples. The test water samples are pre-treated with oxidizing and reducing agents to alter the oxidation state of arsenic to arsenate and arsenite states, respectively. Different color complexes are formed in the test water samples by adding a color reagent (e.g., an ammonium molybdate based acid reagent) that selectively incorporates arsenic according to its oxidation sate, arsenate As (V) or arsenite As (III).

The portable arsenic meter is designed for use in adverse field conditions. The portable arsenic meter may be included a test kit, which can be operated in third world conditions, for example, by people with little or no specialized training, to measure extremely low concentrations of arsenic.

Consideration is now being given to further simplify the use of the portable arsenic meter in the field. In particular, attention is paid to the preparation chemistries utilized to make the arsenic color complexes and the form of chemical reagents used.

SUMMARY OF THE INVENTION

The present invention provides chemical formulations for preparing water samples for measurement of low levels of arsenic contamination using colorimetry. The chemical formulations use chemical reagents in solid forms, which can be easily premeasured and/or premixed for use in the field.

The chemical reagents include an acid reagent for modifying the pH of the water samples; and a solid oxidizing reagent for oxidizing arsenic to an arsenate state. Solid color reagents are used for treating the water samples to make molybdenum-blue color complexes that selectively incorporate arsenic according to its oxidation state. In one formulation, sulfamic acid is used as the acid reagent, and potassium iodate is used as the oxidizing reagent. The color reagent includes sodium molybdate.

Sulfamic acid which is used as an acidifying reagent also advantageously reduces arsenic to the arsenite state. Thus, when the water samples are pretreated with sulfamic acid, reducing agents, which, for example, are used in preparation chemistries based on Johnson and Pilson formulations, are not required to prepare arsenate-free reference samples for differential colorimetry.

BRIEF DESCRIPTION OF THE DRAWINGS

Further features of the invention, its nature, and various advantages will be more apparent from the following detailed description of the preferred embodiments and the accompanying drawings, wherein like reference characters represent like elements throughout, and in which:

FIGS. 1, 2 and 3 show the results of three experimental trials using solid reagents to prepare water samples for dual channel arsenic colorimetry in accordance with the principles of the present invention.

DETAILED DESCRIPTION OF THE PREFERRED EMBODIMENTS

Figure 4:
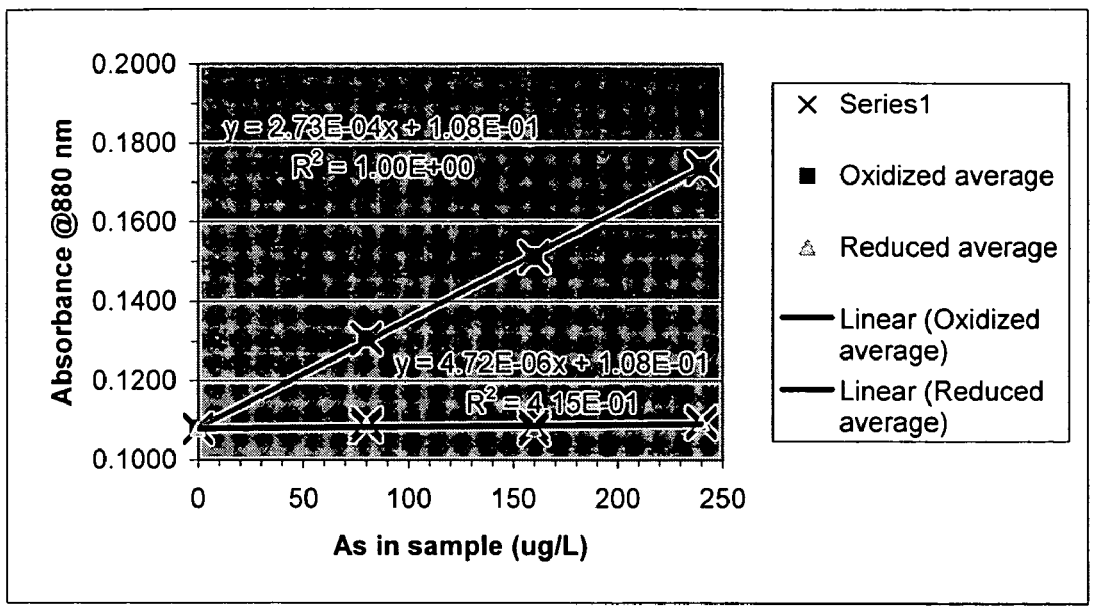
FIGS. 4, 5 and 6 show the data of FIGS. 1, 2 and 3 in graphical form.
Figure 4:
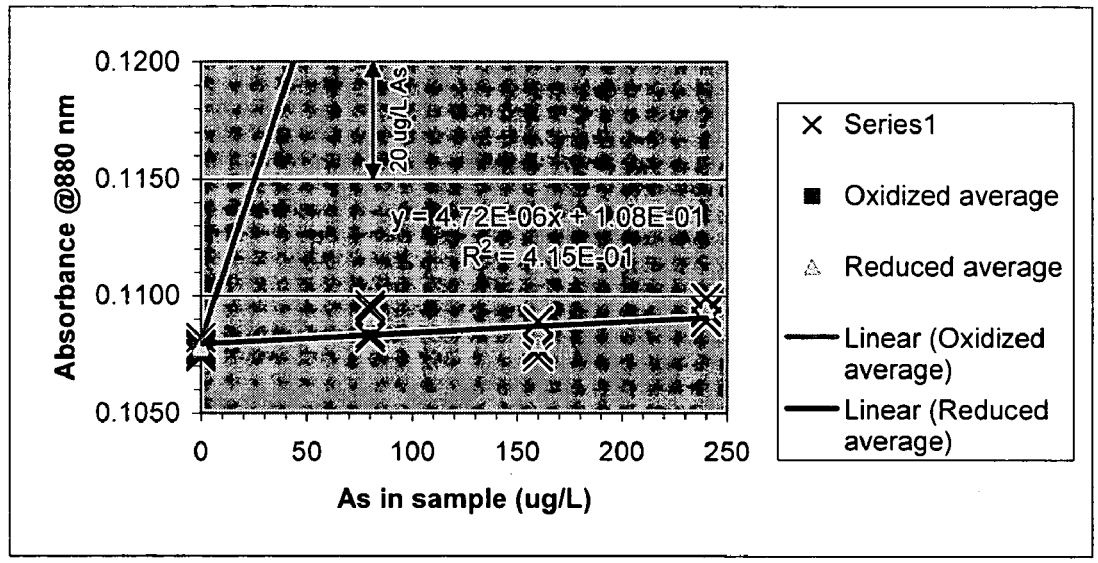

The present invention provides chemical reagent formulations or recipes for preparing water samples for colorimeter measurements of their arsenic content. The formulations have been developed to simplify preparation procedures for quantitative detection of low levels of arsenic contamination in groundwater. The formulations are designed for convenience of use in the field. The chemical reagents selected for the formulations are widely available.

Conventional methods preparation of water samples for colorimetric determination of arsenic concentration, are based on formulations developed by Johnson and Pilson. See e.g., Johnson, D. L. "Simultaneous determination of arsenate and phosphate in natural waters," Environmental Science and Technology, 5, pp. 411-14 (1971); and Johnson, D. L., and M. E. Q. Pilson, "Spectrophotometric determination of arsenite, arsenate, and phosphate in natural waters," Analytica Chimica Acta, 58, 289-299 (1972). International Patent Application No. PCT/US03/026484, incorporated by reference herein, describes a modified Johnson and Pilson formulation that is suitable for preparing groundwater samples containing a large amount of phosphates for differential arsenic colorimetry.

The Johnson and Pilson (or modified) formulations described in the cited references use liquid reducing, oxidizing, and color reagents to prepare water samples for dual channel colorimetry. The reducing reagents (e.g., sodium metabisulfite, sodium thiosulfate and sulfuric acid) are used to reduce arsenic to its arsenite state. Similarly, the oxidizing reagent (e.g., potassium iodate in hydrochloric acid) is used to oxidize arsenic to its arsenate state. The color reagents (e.g., ammonium molybdate, ascorbic acid, antimonyl potassium tartrate and sulfuric acid) are used to selectively incorporate phosphates and arsenic only its arsenate form in molybdenum-blue color complexes. The preparation of the water samples requires careful measurement and dispensing of the liquid reagents in the field. Additionally, the liquid acids must be carefully transported and handled.

In the present formulations, in contrast, all or most of the chemical reagents are advantageously in solid form and can be added directly to a sample. The step whereby reagents must first be dissolved in water is no longer required. The solid reagents may be selected for ease in handling, transport, or local availability. The solid reagents are selected with consideration to the ease with which low molarity dilute solutions necessary for accurate arsenic level detection can be prepared with sufficient precision in the field.

A field test kit may include solid reagents, for example, reagents such as sulfamic acid, potassium iodate, sodium molybdate, and ammonium molybdate salts.

In operation, to measure the arsenic concentration in a water sample, aliquots of water are treated with the solid reagents to develop color complexes (e.g., molybdenum-blue). First, the pH of the water sample is modified (i.e. acidified) by treatment with the acid reagent (e.g., sulfamic acid). Sulfamic acid also effectively reduces any arsenates that are present in the water. An acidified water sample aliquot may be used as the reference aliquot in which only phosphates are incorporated in color complexes upon treatment with suitable color reagents. The use of sulfamic acid in trials shows reproducible results. Thus, a separate reducing step that is used in preparation chemistries based on the Johnson and Pilson formulations to reduce arsenic to an arsenite state is unnecessary. The number of chemical reagents included in arsenic field test kits can be reduced, as conventional reducing agents such as sodium metabisulfite, sodium thiosulfate and sulfuric acid are not required.

Further, a second aliquot of water may be treated with a solid oxidizer to oxidize (or re-oxidize) arsenic in the water to an arsenate state. Solid oxidizers such as potassium iodate have been found to be suitable for this purpose. The oxidizing aliquot of water may then be treated with the color reagents to form color complexes that include both phosphates and arsenates. Dual channel colorimetric measurements of infrared light absorbance in the first and second aliquots then leads to a determination of the arsenic concentration in the manner described in International Patent Application No. PCT/US03/026484.

The solid color reagents included in the present formulation, include for example sodium molybdate, ascorbic acid, antimonyl potassium tartrate. Sodium molybdate has a good solubility, and dissolves quickly without precipitation or residue when added to an acidified water sample. These solid color reagents serve the same purposes as the ammonium molybdate and sulphuric acid based color reagents in the Johnson and Pilson formulations.

Control experiments were carried out to test the efficacy of the present solid chemical reagent formulations for measurement of low levels of arsenic using a portable arsenic calorimeter. In these experiments, the water aliquot size for individual treatment was 125 mL and can be reduced further by applying modern reagent packaging technology to the reagents. The amounts of the (now) all solid oxidation and color reagents utilized in the control experiments were also adjusted in proportion to the reduced aliquot size. The sample reference used in the experiments was de-ionized water spiked to ~5 umol/kg phosphate.

The following trial procedure was employed for preparing water samples for measurement of low levels of arsenic:

Trial Procedure

Acidification Step 1000 g deionized water
spike to 5 umol/L Phosphate (150 uL of 1000 ppm solution)
dissolve 72 g sulfamic acid (8×9 g)
split into eight 125 g aliquots with/without As(V) spikes
each 125 mL aliquot was subsequently processed as follows:

Oxidation Step add 0.005 g potassium iodate (KIO3),
allow to react for 10 min.

Reduction Step

No additional treatment.
Color generation for both oxidized and acidified reference samples
add 0.28 g ascorbic acid
0.007 g K Sb tartrate, and
0.12 g Na molybdate,
allow to react 4 min before then take calorimeter readings every 1 min.

Figure 5:
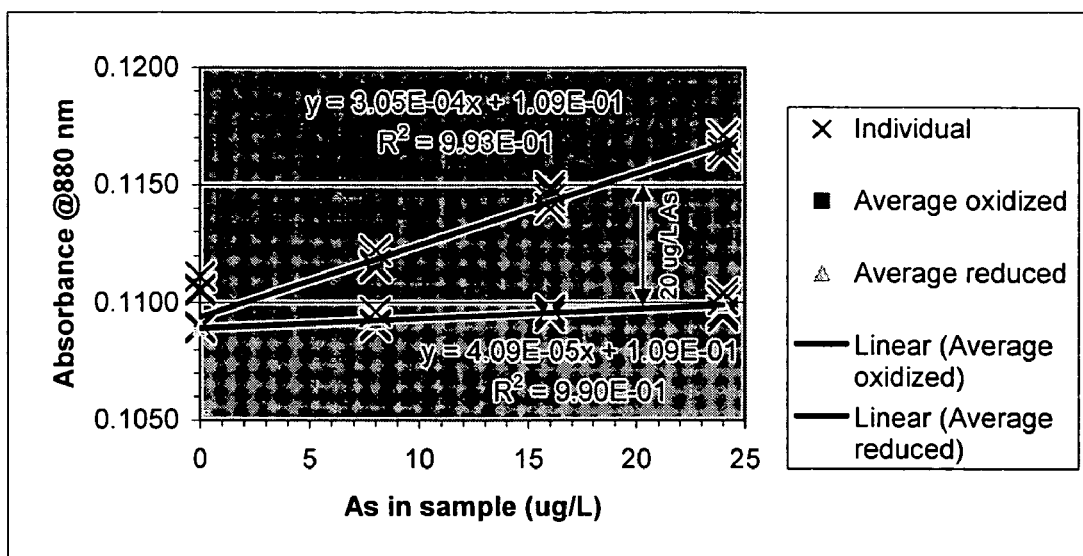
Figure 6:
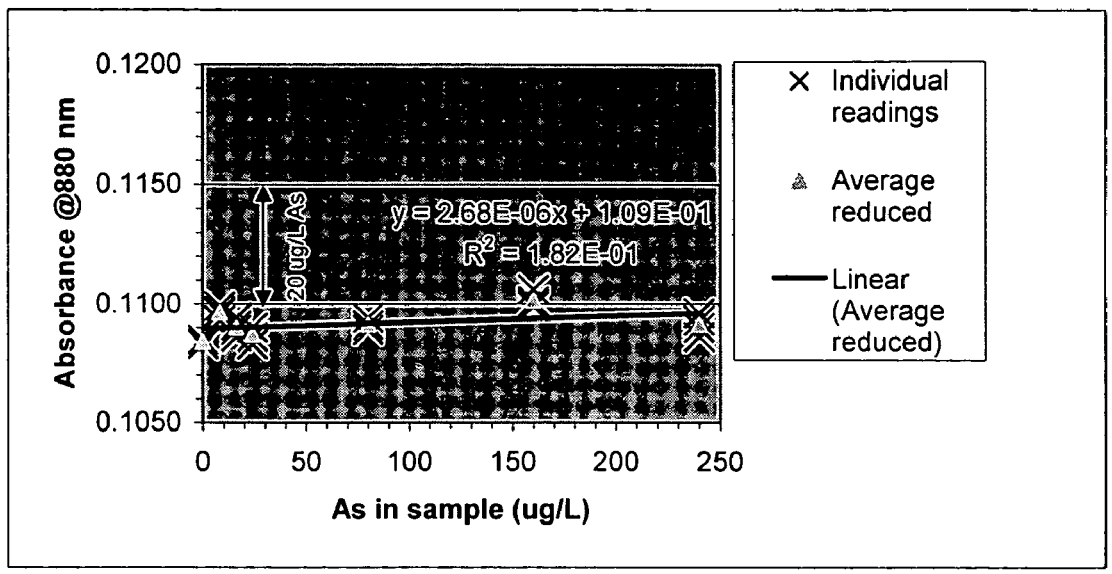

FIGS. 1, 2 and 3 show the results of three sets of experimental measurements absorbance for arsenic concentrations in water ranging from 0 to 240 ug/L. FIGS. 4, 5, and 6 show the absorbance data of FIGS. 1, 2, and 3 in graphical form as a function of the arsenic concentration.

The results indicate that an arsenic detection limit of about 2 ug/L, which may be acceptable for determination of water potability, can be attained using the solid reagent chemistries.

FIGS. 1 and 4 show that the absorbance of oxidized aliquots increases linearly in response to the As spikes of 80, 160, and 240 ug/L while the absorbance of the reference samples remains essentially constant.

FIGS. 2 and 5 show similar results for one order of magnitude lower spikes of 8, 16, and 24 ug/L As. The results are encouraging, although the absorbances for reduced samples indicate a slope suggesting that the As spikes were not completely reduced by the addition of sulfamic acid. FIGS. 3 and 6, however, indicate that the reduction of arsenic to the arsenite state by the addition of sulfamic acid is quite efficient over a wide range of As concentrations.

These results suggest that the solid reagent chemistries of the present invention may be used to reduce the test water sample size required for the portable arsenic meter testing. With additional refinements in procedure, use of the solid reagents may advantageously allow further reductions in the sample cell size designed in portable arsenic colorimeters.

Further, the solid reagents added in the preparation of the test water samples may be premeasured and/or manufactured as premixed pills or tablets. Use of premixed chemical reagents in pill or tablet form can avoid the difficult of weighing or measuring small amounts of reagents in the field (e.g., the amounts of potassium iodate and potassium antimonyl tartrate utilized are on the order of a few mg for a 125 mL water sample).

It will be understood, that the foregoing is only illustrative of the principles of the invention, and that various modifications can be made by those skilled in the art, without departing from the scope and spirit of the invention, which is limited only by the claims that follow.

The invention claimed is:

1. A chemical reagent kit for preparing water samples for colorimetric measurements of arsenic levels in the water samples in the field, wherein the water sample comprises phosphates that have an order of magnitude or more higher concentration than the arsenic concentration, comprising:
   an acid reagent for modifying the pH of the water samples;
   a solid oxidizing reagent for oxidizing arsenic in the water samples to an arsenate state; and
   a solid color reagent for incorporating the arsenic in the arsenate state in the water samples in a color complex.

2. The chemical reagent kit of claim 1 wherein the acid reagent comprises sulfamic acid.

3. The chemical reagent kit of claim 1 wherein the acid reagent when added to a water sample eliminates the need of a further reducing agent that is used in preparation chemistries based on the Johnson and Pilson formulations to reduce arsenic in the water sample to an arsenite state.

4. The chemical reagent kit of claim 1 wherein the solid color reagent comprises a molybdate.

5. The chemical reagent kit of claim 4 wherein the solid color reagent further comprises ascorbic acid.

6. The chemical reagent kit of claim 1 wherein the solid color reagent comprises a molybdate and an antimonyl tartrate.

7. The chemical reagent kit of claim 1 comprising premeasured and premixed solid reagents in pill form.

8. The chemical reagent kit of claim 1, wherein the constituents are such that when added to the water sample having phosphates in an order of magnitude or more higher concentration than the arsenic concentration:

the acid reagent acidifies the water sample;

the solid oxidizing reagent oxidizes arsenic in the water samples to an arsenate state; and the solid color reagent incorporates the arsenic in the arsenate state in the water sample in a color complex and forms such color complex in a sufficient quantity so that a measurable, differential light absorbance of the color complex with respect to a reference acidified water sample aliquot yields the arsenic concentration in the water sample having phosphates in an order of magnitude or more higher concentration than the arsenic concentration.

9. The chemical reagent kit of claim 8, wherein the solid color reagent incorporates the arsenic in the arsenate state in the water sample in a color complex and forms such color complex in a sufficient quantity so that differential light absorbance of the color complex is measurable by a low voltage, portable colorimeter.

* * * * *

UNITED STATES PATENT AND TRADEMARK OFFICE
CERTIFICATE OF CORRECTION

| | | |
|---|---|---|
| PATENT NO. | : 7,315,375 B2 | Page 1 of 1 |
| APPLICATION NO. | : 11/006284 | |
| DATED | : January 1, 2008 | |
| INVENTOR(S) | : Van Geen | |

It is certified that error appears in the above-identified patent and that said Letters Patent is hereby corrected as shown below:

Column 1, line 14, please insert the following header and paragraph:

-- Statement Regarding Federally Sponsored Research or Development
This invention was made with government support under grant number ES010349 awarded by the National Institutes of Health. The government has certain rights in the invention. --

Signed and Sealed this

Twenty-fourth Day of June, 2008

JON W. DUDAS
*Director of the United States Patent and Trademark Office*